United States Patent
Newcomb et al.

(10) Patent No.: US 8,284,305 B2
(45) Date of Patent: Oct. 9, 2012

(54) SYSTEM AND METHOD FOR ACQUIRING IMAGES

(75) Inventors: David Newcomb, Morrisville, NC (US); Demetris P. Young, Durham, NC (US)

(73) Assignee: Parata Systems, LLC, Durham, NC (US)

(*) Notice: Subject to any disclaimer, the term of this patent is extended or adjusted under 35 U.S.C. 154(b) by 376 days.

(21) Appl. No.: 12/623,878

(22) Filed: Nov. 23, 2009

(65) Prior Publication Data

US 2010/0128165 A1   May 27, 2010

Related U.S. Application Data

(60) Provisional application No. 61/118,014, filed on Nov. 26, 2008.

(51) Int. Cl.
   *H04N 5/225* (2006.01)
(52) U.S. Cl. ........................ 348/373; 348/131
(58) Field of Classification Search ............. 348/86–95, 348/125–134, 207.99, 370, 373–376; 382/110, 382/141–152, 163, 165; 356/239.4, 240.1; 250/223 B; 235/462.42; 362/247
See application file for complete search history.

(56) References Cited

U.S. PATENT DOCUMENTS

| | | | | |
|---|---|---|---|---|
| 4,731,649 A | * | 3/1988 | Chang et al. | 348/127 |
| 5,030,823 A | * | 7/1991 | Obdeijn | 250/223 B |
| 5,220,400 A | * | 6/1993 | Anderson et al. | 356/240.1 |
| 5,457,492 A | * | 10/1995 | Sasaki et al. | 348/126 |
| 6,273,338 B1 | * | 8/2001 | White | 235/462.42 |
| 6,535,637 B1 | | 3/2003 | Wootton et al. | |
| 6,542,238 B1 | | 4/2003 | Tsuboi et al. | |
| 6,554,452 B1 | * | 4/2003 | Bourn et al. | 362/247 |
| 7,028,723 B1 | | 4/2006 | Alouani et al. | |
| 7,477,374 B2 | * | 1/2009 | Schmidt et al. | 356/239.4 |
| 2002/0114505 A1 | * | 8/2002 | Mahon et al. | 382/145 |
| 2005/0220335 A1 | | 10/2005 | Budd | |

FOREIGN PATENT DOCUMENTS

| | | |
|---|---|---|
| DE | 10 2004 016 829 A1 | 11/2005 |
| WO | WO 02/25568 A2 | 3/2002 |

OTHER PUBLICATIONS

Partial International Search Report for PCT/US2009/065617 mailed Jun. 4, 2010.
International Search Report for PCT/US2009/065617 mailed Mar. 8, 2011.

* cited by examiner

*Primary Examiner* — Nelson D. Hernández Hernández
*Assistant Examiner* — Dennis Hogue
(74) *Attorney, Agent, or Firm* — Myers Bigel Sibley & Sajovec

(57) ABSTRACT

A vision system useful in acquiring images includes: a light dome having a window and a perimeter; an annular light curtain positioned within and radially inwardly from the perimeter of the light dome such that an annular gap is formed between the light dome and the light curtain; and a light ring positioned to illuminate the gap between the light dome and the light curtain. The light curtain and window are sized and positioned such that no direct light from the light ring reaches the window. The system further comprises a camera having a lens facing the window to acquire images of an object on a side of the window opposite the camera. The images acquired by the camera can then be compared to stored images to determine whether the identity of the objects (which may be pharmaceutical tablets) is as expected.

8 Claims, 4 Drawing Sheets

SYSTEM AND METHOD FOR ACQUIRING IMAGES

RELATED APPLICATION

This application claims priority from U.S. Provisional Patent Application Ser. No. 61/118,014, filed Nov. 26, 2008, the disclosure of which is hereby incorporated herein in its entirety.

FIELD OF THE INVENTION

The present invention is directed generally to the identification of pharmaceuticals, and more particularly to the automatic identification of dispensed pharmaceuticals.

BACKGROUND OF THE INVENTION

There is an ongoing and predicted long-term shortage of licensed pharmacists. Due to the increasing age of the population and the ever-increasing number of prescription medicines available, the demand for prescription drugs is growing at rate that will far exceed the capacity and numbers of licensed pharmacists. The net impact of this imbalance is that pharmacists are increasingly spending more time doing clerical and administrative tasks such as verifying filled prescriptions and checking data entry done by pharmacy technicians. Since the capacity of any one pharmacist is fixed, the output of a pharmacy has become constrained. Consequently, the labor and total cost per prescription continues to rise. The December 2000 Department of Health and Human Services Report to Congress titled "The Pharmacist Workforce: A Study of the Supply and Demand for Pharmacists", which is hereby incorporated herein by reference, provides an overview of the above problem.

Due to these increased demands on a pharmacist's time, and the resulting increased reliance on technicians and other non-professional staff to fill prescriptions, there is an increased chance for prescription error. While these errors may take many forms, the likelihood of a dangerous or life threatening "adverse drug event" increases proportionally with the increased chance of prescription fill error. Several studies have shown that prescription error rates are consistently in the 2% to 7% range, with a 4% error rate often cited as a reliable average. The number of deaths due to medication errors is estimated to exceed 7,000 per year in the United States alone. Of course, this number does not include non-fatal conditions from drugs that also result in some form of trauma or injury. The resulting litigation costs associated with these prescription fill errors have also dramatically increased.

Many existing pharmacy filling systems and procedures still require a human operator, whether that operator is a technician or a licensed pharmacist, to validate visually whether the drug that is delivered to the customer is correct. Thus, the human factor can contribute to the majority of prescription fill errors. Existing visual verification techniques rely on comparing an electronic image of the prescribed medication, i.e., a picture of the prescribed medication retrieved from a data library, with the actual medication that is dispensed for the patient. Other systems and procedures rely on comparing the dispensed medication with that in the original manufacturer's supply container, or comparing an electronic image of the filled prescription with an electronic image of the prescribed medication retrieved from a data library.

Each of these verification systems present similar problems. First, these known verification methods assume that all drugs are visually distinct. This assumption causes many problems because many drugs are not, in fact, visually distinct and, in other cases, the visual differences between drugs is very subtle. For instance, manufacturers are rapidly exhausting unique shapes, colors and sizes for their solid dosage form products. To further complicate the problem, generic drug manufactures may be using shapes, colors, and sizes that are different than that of the original manufacturer. Second, even though some known systems may utilize a National Drug Code (NDC) bar code to verify that the supply bottle being accessed corresponds correctly to the patient's prescription, a fraction of filled prescriptions that are never picked up are returned to the supply shelves for reuse in later prescriptions. These reused bottles will not, therefore, have a manufacturer's bar code on them. It is, therefore, difficult, if not impossible, to incorporate such validation schemes for these unused prescriptions. Furthermore, in these circumstances, a supply bottle is not available for a visual comparison with the filled prescription. Finally, each of these known manual verification and validation techniques typically requires that the pharmacist spend a significant portion of his day performing these administrative or clerical tasks and allows less time for patient consultation and other professional pharmacist activities.

Many solid dosage pills tend to have visually distinct features. As described in U.S. Pat. No. 6,535,637 to Wootton, the disclosure of which is hereby incorporated herein by reference, one vision-based system takes an image of the dispensed pills and processes the image to obtain a set of characteristic features of the pill. These features may include the coloration, shape, size, and any surface features of the pills. These features are then automatically compared with those of all the pills which can be dispensed by a dispensing apparatus. If a pill can be uniquely identified as the correct pill, the container of pills is accepted. Otherwise, the container is rejected. If, as a result of the processing, a determination cannot be made, the container is provisionally rejected and is subsequently inspected by a pharmacist to determine if the prescription is correctly filled.

Because in many pharmacies throughput of prescriptions is important, it may be desirable to increase the speed of analysis. This may be possible by analyzing a filled, capped container rather than an uncapped container such as that disclosed in Wootton. However, many pharmaceutical containers are transparent with an amber color. The amber coloration of the vial can tint the pills in the vial when an image is taken through the wall of the vial, thereby providing an inaccurate color for the image. Also, because multiple types of vials are used in pharmaceutical dispensing, the degree of amber coloration may differ from vial to vial. Further, in some instances different colors of vials (e.g., red, green, blue) may be used. It may be desirable to address some of these issues to provide a vision-based discrimination system that can operate on a filled, capped vial.

SUMMARY OF THE INVENTION

As a first aspect, embodiments of the present invention are directed to a vision system that may be useful in acquiring images. The imaging system comprises: a light dome having a window and a perimeter; an annular light curtain positioned within and radially inwardly from the perimeter of the light dome such that an annular gap is formed between the light dome and the light curtain; and a light ring positioned to illuminate the gap between the light dome and the light curtain. The light curtain and window are sized and positioned such that no direct light from the light ring reaches the window. The system further comprises a camera having a lens facing the window to acquire images of an object on a side of the window opposite the camera. The images acquired by the camera can then be compared to stored images to determine whether the identity of the objects (which may be pharmaceutical tablets) is as expected.

As a second aspect, embodiments of the present invention are directed to a method of acquiring an image of objects within a transparent, colored container. The method comprises: determining the expected identity of the objects in the container; selecting a light color based on the expected identity; illuminating the container and the objects therein with light of the selected color; and acquiring an image of the objects within the container.

As a third aspect, embodiments of the present invention are directed to a method of acquiring an image of objects within a transparent, colored container, comprising: detecting the RGB values of the color of the container; automatically determining the inverse RGB values of the color of the container; illuminating the container and the objects therein with light having substantially the inverse RGB values of the color of the container; and acquiring an image of the objects within the container.

As a fourth aspect, embodiments of the present invention are directed to a method of acquiring an image of objects within a transparent, colored container, comprising: detecting the RGB values of the color of the container; manually determining the inverse RGB values of the color of the container; illuminating the container and the objects therein with light having substantially the inverse RGB values of the color of the container; and acquiring an image of the objects within the container.

DETAILED DESCRIPTION OF EMBODIMENTS OF THE INVENTION

Figure 1:
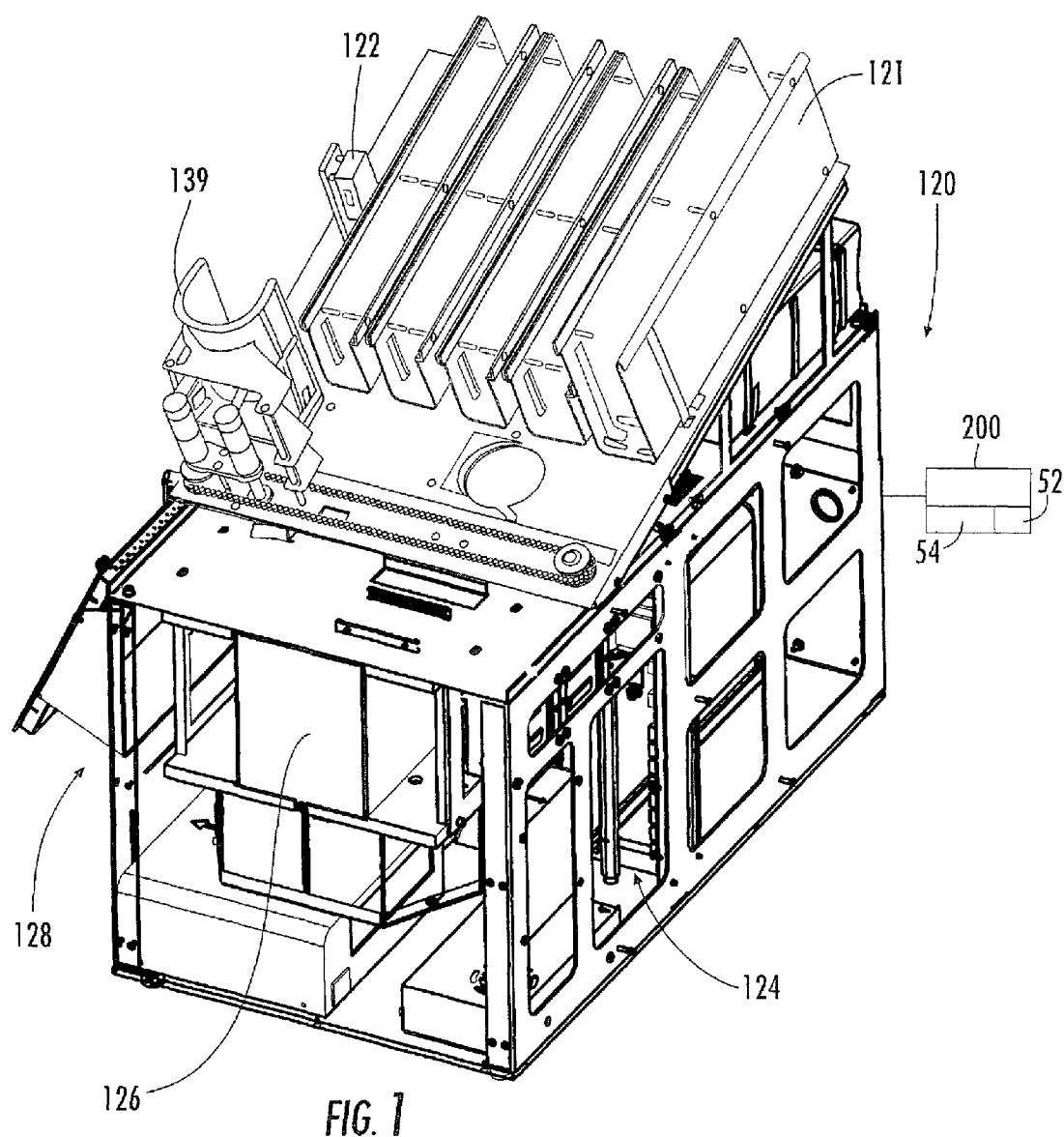
FIG. 1 is a front perspective view of an automated pharmaceutical verification system that includes a vision system according to embodiments of the present invention.

The present invention will now be described more fully hereinafter, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. In the drawings, like numbers refer to like elements throughout. Thicknesses and dimensions of some components may be exaggerated for clarity.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein the expression "and/or" includes any and all combinations of one or more of the associated listed items.

In addition, spatially relative terms, such as "under", "below", "lower", "over", "upper," "front," "rear" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

Well-known functions or constructions may not be described in detail for brevity and/or clarity.

Turning now to the figures, FIG. 1 illustrates a pharmaceutical verification system 120 according to embodiments of the present invention. The system 120 includes a vial loading station 121, bar code scanning or RFID reading station 122, a vision station 124, a spectroscopy station 126, a stamping station 128, and an offload station located underneath the vial loading station 121 (not visible in FIG. 1). Vials are moved between these stations with a sliding conveyor 139 adjacent the bar code scanning station and a wheel conveyor (not shown). A controller 200 controls the operation of the various stations and the conveyor. The operation of the system 120 is described in greater detail in co-pending and co-assigned U.S. Provisional Patent Application Ser. No. 61/118,006, filed Nov. 26, 2008, and U.S. patent application Ser. No. 12/623,917, entitled System and Method for Verifying the Contents of a Filled, Capped Pharmaceutical Prescription and filed concurrently, the disclosure of each of which is hereby incorporated herein in its entirety.

Figure 2:
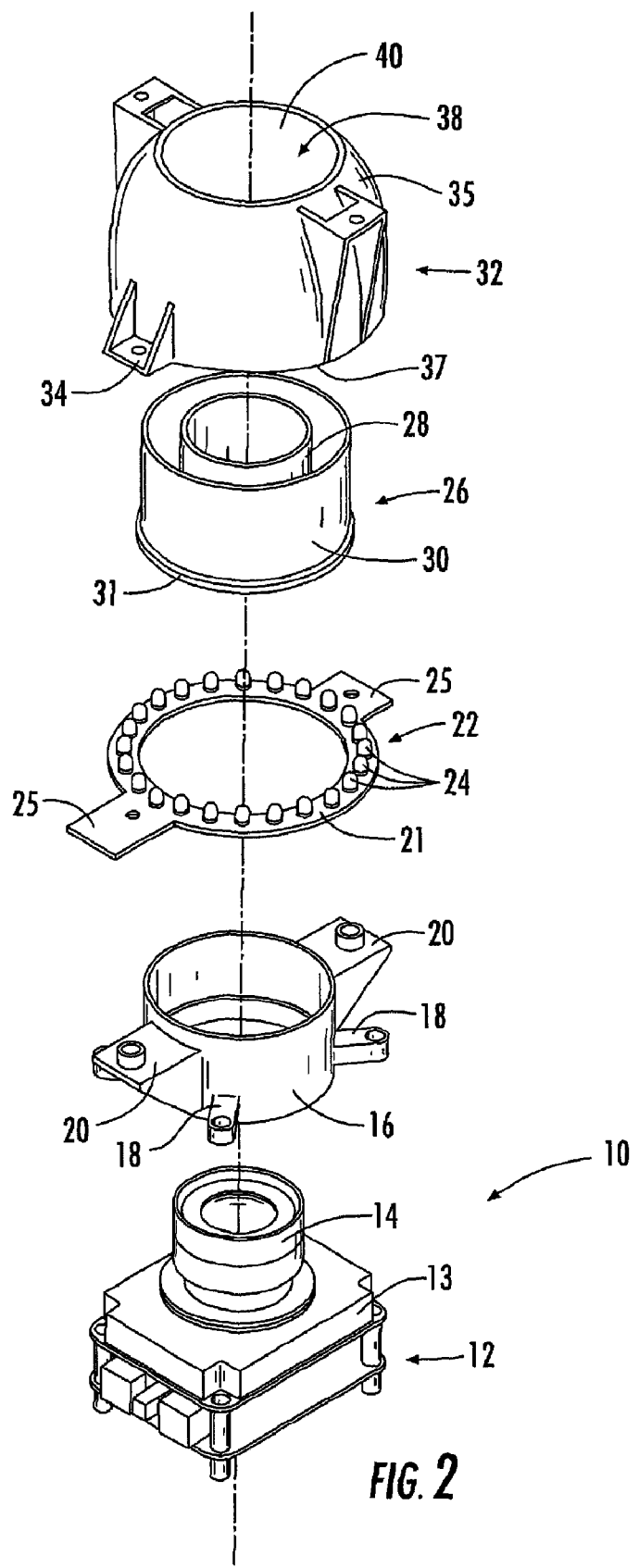
FIG. 2 is an exploded view of the vision system of the pharmaceutical verification system of FIG. 1.
Figure 3:
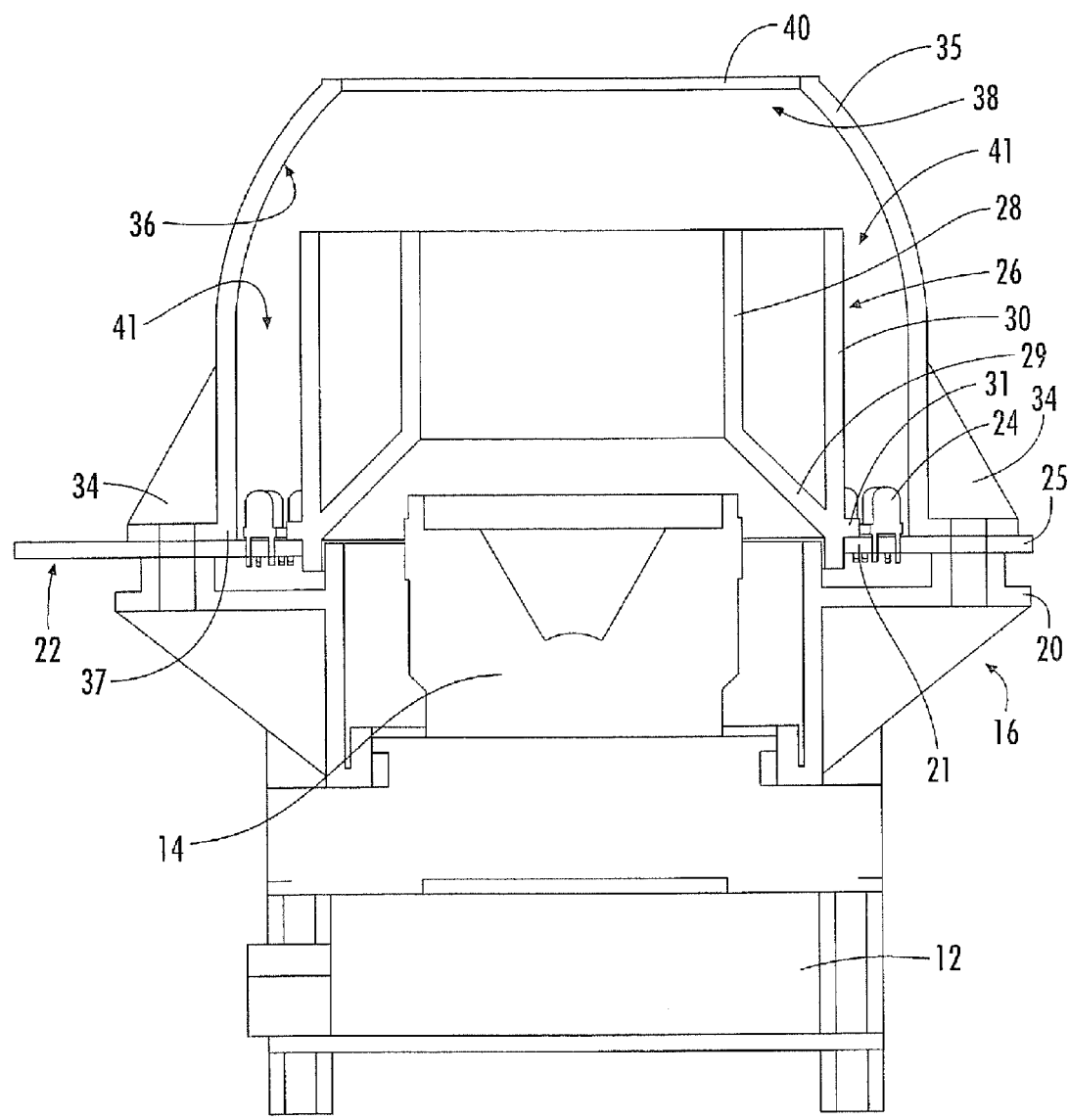
FIG. 3 is a side section view of the vision system of FIG. 2.

Turning now to FIGS. 2 and 3, an imaging system for use in the vision station 124, designated broadly at 10, is shown therein. The system 10 includes a camera 12, a light ring 22, a light curtain 26, and a light dome 32. Each of these components is described in greater detail below.

The camera 12 can be any camera that is suitable for the acquisition of digital images. An exemplary camera 12 is Model No. Lw570C, available from Lumenera Corp., Ottawa, Canada. As shown in FIGS. 2 and 3, the camera 12 is mounted such that its lens 14 faces upwardly from its body 13. A sleeve 16 rests on the upper surface of the body 13 and circumferentially surrounds the lens 14. The sleeve 16 includes radially-extending tabs 18 that are used to mount the sleeve 16 to the camera 12, and also includes two flanges 20 that extend radially from diametrically opposed sections of the upper edge of the sleeve 16.

Referring still to FIGS. 2 and 3, the light ring 22 has a generally annular and planar body portion 21. Tabs 25 extend radially from diametrically opposed sections of the body portion 21 and are used to provide mounting locations for the light ring 22 on top of the sleeve 16. A series of light emitting diodes (LEDs) 24 are mounted on the upper surface of the body portion 21. The LEDs 24 are alternating red/green/blue (RGB) LEDs that produce corresponding RGB wavelengths using a conventional RGB color scheme to produce white light. The LEDs 24 are adjustable in intensity, such that the intensity of red, green and/or blue light can be varied. As such, the color of light emanating from the light ring 22 can be adjusted as desired. Intensity and wavelength levels of red, green and blue light that can be employed to produce a particular shade of light are known to those of skill in this art and need not be detailed herein.

Referring again to FIGS. 2 and 3, the light curtain 26 includes an annular inner wall 28 and a concentric outer wall 30. A beveled surface 29 (FIG. 3) joins the lower edges of the inner and outer walls 28, 30. A radial lip 31 extends outwardly from the outer wall 30 and rests on the inner edge of the body portion 21 of the light ring 22. This placement of the lip 31 positions the outer wall 30 radially inward of the LEDs 24. The inner wall 28 is positioned above and generally axially aligned with the lens 14 of the camera 12.

Still referring to FIGS. 2 and 3, the light dome 32 is generally bowl-shaped, with a dome wall 35 having an opening 38 in its upper portion and a perimeter 37 at its lower edge. A clear glass window 40 fills the opening 38. Flanges 34 (only one of which is shown in FIG. 2) extend radially outwardly from diametrically opposed sections of the lower edge of the dome wall 35 and align with the flanges 20 of the sleeve 16 and the tabs 25 of the light ring 22. Fasteners can be inserted through the flanges 34, the tabs 25 and the flanges 20 to fasten the light dome 32, the light ring 22, and the sleeve 16 together.

Referring now to FIG. 3, the inner surface 36 of the dome wall 35 and the outer wall 30 of the light curtain 26 form an annular gap 41 through which light from the LEDs 24 can pass. The dome wall 35 has sufficient curvature that the edges of the window 40 are radially inward of the upper edges of the outer wall 30; as a result, light from the LEDs 24 cannot shine directly onto the window 40. Also, the inner surface 36 is typically formed of an anti-glare material or treated with an anti-glare coating (such as a flat white paint) to reduce or minimize specular reflection and/or increase or maximize diffuse reflection.

Figure 4:
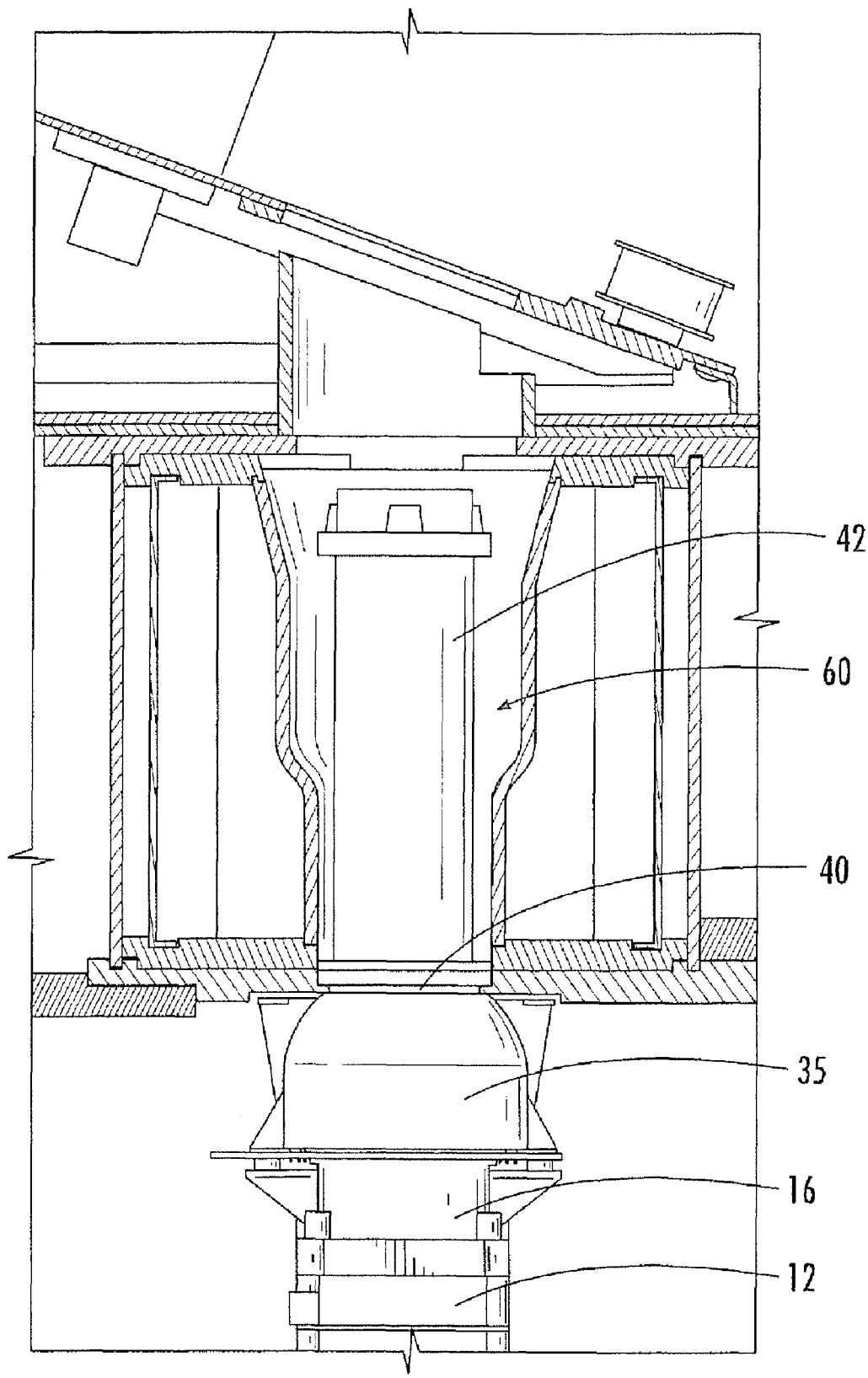
FIG. 4 is a side section view of the vision system of FIG. 2 showing a vision compartment within the pharmaceutical verification system of FIG. 1 containing a vial.

Turning now to FIG. 4, the system 10 will ordinarily be employed with a chamber, such as chamber 60, in which resides the object (in this instance a pharmaceutical vial 42) for imaging. The chamber 60 is typically light-tight, such that the only appreciable light entering the chamber 60 enters through the window 40. In some embodiments, the chamber 60 will include a trap door or cover that allows the insertion of the object into the chamber but closes to prevent light from entering.

Referring back to FIG. 1, a controller 200 is connected to the camera 12 and the light ring 22. The controller 200 includes a memory 52 (either local or remote) that has stored image data for multiple pharmaceutical tablets. The controller 200 also has a processor 54 that enables an image taken by the camera 12 to be compared to the stored image data to determine whether one or more visual features or attributes of the dispensed pharmaceutical match a pharmaceutical stored in the memory 52.

In operation, as shown in FIG. 4 a vial 42 (typically a capped vial) containing a dispensed pharmaceutical is deposited in the chamber 60 and rests with its lower end on the window 40. The controller 200 activates the LEDs 24 of the light ring 22. Light from the LEDs 24 travels through the gap 41 to the inner surface 36 of the dome wall 35. However, because of the location of the outer wall 30 of the light curtain 26 and the position of the window 40, none of the light from the LED reaches the window 40 directly; instead, light reaching the window 40 (and, in turn, the vial 42 and the tablets residing therein) is indirect light, which produces little to no glare. This indirect light illuminates the vial 42 and tablets sufficiently for an image to be taken with the camera 12. The controller 200 then stores the image for subsequent processing, comparison to a known image, and/or other tasks.

It should be noted that, due to the adjustable nature of the LEDs 24 of the light ring 22, the color of light illuminating the vial 42 and tablets can be selected for advantageous imaging. For example, as discussed in co-pending and co-assigned U.S. patent application Ser. No. 12/249,402, filed Oct. 10, 2008, the disclosure of which is hereby incorporated herein by reference, images of tablets contained in a transparent amber-colored vial and acquired through the wall of the vial may exhibit substantially the same color as the tablets themselves when the vial is illuminated with light of a "reverse" color. As discussed in detail in the cited patent application, a "reverse" color is one that uses reciprocal values for red, green and blue in an RGB system. The use of light that is the reverse color of a transparent amber vial (e.g., a bluish hue for an amber vial) can enable images of objects in the vial, wherein the images are acquired through the walls of the vial, to exhibit the same color as the objects would exhibit without the vial. Thus, the LEDs 24 of the light ring 22 can be adjusted to produce light having a "reverse" color to that of the vial (again, as an example, a bluish light for an amber-colored vial).

In one embodiment, the light color can be determined by first taking an image of the vial 42 with the camera 12. A histogram of that image can be produced. The inverse color of the histogram can then be determined, and the controller 200 can, through the LEDs 24 of the light ring 22, generate light of the inverse color.

In other embodiments, a sensor (not shown) may be included in the vision system 10 to detect the color of the vial 42. The sensor can transmit signals regarding the color of the vial 42 to the controller 200, which then induces the LEDs 24 of the light ring 22 to produce light of a "reverse" color to that of the vial 42. In such an embodiment, the system 10 can "tune" the light emitted from the LEDs 24 to account for differently-colored vials or variations in color due to different manufacturers, different lots, or the like.

Also, in some embodiments, the controller 200 may, in view of the identity of the prescribed pharmaceutical labeled on the vial (typically in bar code form), adjust the light produced by the LEDs 24 of the light ring 22 to a color that is particularly advantageous for distinguishing the prescribed pharmaceutical from a similar pharmaceutical. Thus, in those embodiments the color of the light may be one that is not substantially the reverse color of the vial, but is advantageous for detection of the particular pharmaceutical in the particular vial by most greatly enhancing the differences from the similar pharmaceutical.

Those skilled in this art will appreciate that color schemes other than RGB may be employed. In addition, in some embodiments electromagnetic radiation outside of the visible light range, such as ultraviolet or infrared, may also be employed.

The foregoing is illustrative of the present invention and is not to be construed as limiting thereof. Although exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention. The following claims are provided to ensure that the present application meets all statutory requirements as a priority application in all jurisdictions and shall not be construed as setting forth the scope of the invention.

That which is claimed is:

1. An imaging system, comprising:
   a light dome having a window at an upper end thereof and a perimeter;
   an annular light curtain positioned within and radially inwardly from the perimeter of the light dome such that an annular gap is formed between the light dome and the light curtain, the light curtain including annular outer and inner walls and a surface that joins the outer and inner walls, the inner and outer walls extending upwardly from the surface; and
   a light ring positioned to illuminate the gap between the light dome and the light curtain;
   wherein the light curtain and window are sized and positioned such that no direct light from the light ring reaches the window; and
   a camera having a lens facing the window to acquire images of an object on a side of the window opposite the camera, the lens positioned below an upper end of the inner wall of the light curtain.

2. The imaging system defined in claim 1, wherein the light ring comprises a plurality of light emitting diodes (LEDs).

3. The imaging system defined in claim 2, wherein the plurality of LEDs comprises LEDs of at least three different wavelengths.

4. The imaging system defined in claim 1, wherein the inner wall is dimensioned to have generally the same radius as the lens, and wherein the outer wall has a diameter that is less than a diameter defined by the light ring.

5. The imaging system defined in claim 1, further comprising a controller associated with the light ring to control the color produced by the light ring.

6. The imaging system defined in claim 5, wherein the controller is configured to select the color of light produced by the light ring based on the color of the object.

7. The imaging system defined in claim 5, wherein the controller is configured to select the color of light produced by the light ring based on an expected identity of the object.

8. The imaging system defined in claim 1, wherein the light dome includes an anti-glare coating.

\* \* \* \* \*